United States Patent [19]
Davidson

[11] Patent Number: 5,994,512
[45] Date of Patent: Nov. 30, 1999

[54] ANTIBODY DERIVATIVES FOR CONTROLLING GENE EXPRESSION

[75] Inventor: Eric H. Davidson, Pasadena, Calif.

[73] Assignee: California Institute of Technology, Pasadena, Calif.

[21] Appl. No.: 09/118,845

[22] Filed: Jul. 20, 1998

Related U.S. Application Data

[62] Division of application No. 08/919,002, Aug. 27, 1997, Pat. No. 5,783,420, which is a division of application No. 08/660,275, Jun. 7, 1996, Pat. No. 5,712,379.

[51] Int. Cl.$^6$ .................................................. C07K 16/46
[52] U.S. Cl. ......................................................... 530/387.3
[58] Field of Search .......................................... 530/387.3

[56] References Cited

PUBLICATIONS

Beerli, R.R., et al., "Autocrine Inhibition of the Epidermal Growth Factor Receptor by Intracellular Expression of a Single–Chain Antibody," *Biochemical and Biophysical Research Communications* 204(2):666–672 (1994).

Beerli, R.R., et al., "Intracellular Expression of a Single Chain Antibodies Reverst ErbB–2 Transformation," *The Journal of Biological Chemistry*, 269(39):23931–23936 (1994).

Biocca, S., et al., "Expression and Targeting of Intracellular Antibodies in Mammalian Cells," *The EMBO Journal*, 9(1):101–108 (1990).

Kabat, E.A., Recombination of Separated Chains to Form IgG, *Structural Concepts in Immunology and Immunochemistry* (2nd Ed.), Holt, Rinehart ad Winston:New York (1976) pp. 248–252.

Marasco, W.A., et al., "Design, Intracellular Expression, and Activity of a Human Anti–Human Immunodeficiency Virus Type 1 gp120 Single–Chain Antibody," *Proc. Natl. Acad. Sci. USA*, 90:7889–7893 (1993).

Biocca et al. Expression and targetingt of intracellular antibodies in mammalian cells. EMBO J. vol. 9 pp. 101–108, 1990.

*Primary Examiner*—John S. Brusca
*Attorney, Agent, or Firm*—Dolly A. Vance; Flehr Hohbach Test Albritton & Herbert LLP

[57] ABSTRACT

The present invention is directed to methods and compositions useful for altering the transcriptional expression of genes in eukaryotic cells. The invention employs novel antibody derivative molecules which function to recognize and bind to specific cis-regulatory DNA sequence elements of a eukaryotic gene. When two antibody derivative molecules are bound to adjacent cis-regulatory DNA sequence elements of a gene, those molecules may interact to form an antibody binding site which is capable of recognizing and binding to a transcription factor protein for the target gene, thereby affecting the functionality of that transcription factor protein and, in turn, the transcriptional activity of the gene. Also provided herein are isolated nucleic acids encoding the novel antibody derivative molecules of the present invention and expression vectors comprising those nucleic acids.

7 Claims, 1 Drawing Sheet

ANTIBODY DERIVATIVES FOR CONTROLLING GENE EXPRESSION

This is a division of application Ser. No. 08/919,002 filed Aug. 27, 1997, U.S. Pat. No. 5,783,420, which application is a divisional of U.S. Ser. No. 08/660,275, filed Jun. 7, 1996, U.S. Pat. No. 5,712,379.

FIELD OF THE INVENTION

The present invention is directed to methods and compositions useful for affecting gene expression in eukaryotic cells.

BACKGROUND OF THE INVENTION

Eukaryotic cells are capable of controlling gene expression and the synthesis of proteins through a variety of different regulatory mechanisms. These regulatory mechanisms include, for example, regulatory control at the level of gene transcription, control over RNA processing and transport within the cell, control over mRNA degradation, control over mRNA translation and control over the activity of proteins once they have been synthesized By far the most important of the eukaryotic regulatory control mechanisms described above, however, is the regulation of gene expression and protein synthesis at the transcriptional level. In fact, only regulatory control of gene expression at the transcriptional level ensures that no superfluous RNA or protein intermediates are synthesized.

The regulation of eukaryotic gene expression and protein synthesis at the transcriptional level generally involves both cis-regulatory DNA sequence elements, which are often located near the transcription initiation site of any gene of interest, and trans-acting transcription factor proteins. In the most general case, eukaryotic gene transcriptional activity is regulated by the sequence-specific binding of trans-acting transcription factor proteins to specific cis-regulatory DNA sequence elements. Then, depend ing upon whether the trans-acting transcription factor proteins are "positive" or "negative" transcription al regulators, the sequence-specific binding of those trans-acting transcriptional factor proteins to their respective cis-regulatory DNA sequence elements will act to either increase or decrease the transcriptional activity of the gene with which those cis-regulatory DNA sequence elements are associated.

Numerous effort s have been made to manipulate the transcriptional activity of eukaryotic genes in vivo. Many of these efforts have concentrated on attempting to interfere with the binding of various DNA binding proteins to their respective cis-regulatory DNA sequence elements, thereby affecting the ability of those DNA binding proteins to either activate or suppress transcription from the target gene. These efforts, however, have proven, for the most part, to be less than successful. Moreover, many of these methods result in adverse consequences such as, for example, altering the express ion of more than just the desired gene.

Thus, there is a need for novel methods and compositions which are useful for altering the transcriptional expression of one or more target genes in eukaryotic cells without significantly affecting the transcriptional expression of other cellular genes. Accordingly, it is an object of the present invention to provide novel methods for altering the expression of a eukaryotic gene without significantly affecting the expression of other cellular genes. It is also an object of the present invention to provide novel compositions for use in methods for affecting the transcription of eukaryotic genes in vivo.

SUMMARY OF THE INVENTION

The present invention is directed to methods for altering the expression of a single gene in a eukaryotic cell wherein expression of that gene is under the regulatory control of at least three closely-situated cis-regulatory DNA sequence elements. The method comprises introducing into a eukaryotic cell at least an expression vector which encodes at least first and second antibody derivatives which are expressed and transported into the nucleus of the cell, wherein the first and second antibody derivative molecules specifically bind to adjacent first and second cis-regulatory DNA sequence elements of the gene and, once bound, interact to form an antibody binding site for a transcription factor protein that is capable of specifically binding to a third cis-regulatory DNA sequence element of the target gene. Binding of the transcription factor protein by the newly formed antibody binding site, in turn, effectively reduces binding of the transcription factor to its third cis-regulatory DNA sequence element on the target gene, thereby affecting the transcriptional expression of that target gene. The transcription factor protein of interest can be a positive regulator of gene expression, wherein interference with its binding to its specific cis-regulatory DNA sequence element would be expected to decrease expression of the target gene. On the other hand, the transcription factor protein of interest may be a negative regulator of gene expression, wherein interference with its binding to its specific cis-regulatory DNA sequence element would be expected to increase expression of the target gene.

The present invention is further directed to antibody derivative molecules which are capable of specifically binding to a first cis-regulatory DNA sequence element of a eukaryotic gene, wherein the antibody derivative molecules comprise (1) an N-terminal nuclear localization signal which allows the antibody derivative molecule to be transported into the nucleus of the cell after it is expressed in the cytoplasm, (2) a light chain or heavy chain variable region of an antibody molecule, wherein the antibody from which the variable region is derived is capable of specifically binding to a transcription factor protein of interest, and (3) a C-terminal DNA binding domain which is derived from a protein that is capable of specifically binding to said first cis-regulatory DNA sequence element. Optionally, the antibody derivative molecules of the present invention may also comprise an amino acid linker segment which functions to separate the antibody variable region and the C-terminal DNA binding domain. Moreover, the antibody derivative molecules of the present invention may also comprise an antigenic epitope which is capable of detection in the nucleus of a eukaryotic cell and which can be used as a marker for the quantitative assessment of nuclear localization of the antibody derivative molecule.

The present invention is also directed to isolated nucleic acid molecules encoding antibody derivatives and replicable expression vectors comprising such nucleic acid molecules operably linked to control sequences recognized by a host cell transformed with the vector.

DETAILED DESCRIPTION OF THE INVENTION

A. Definitions

Figure 1:
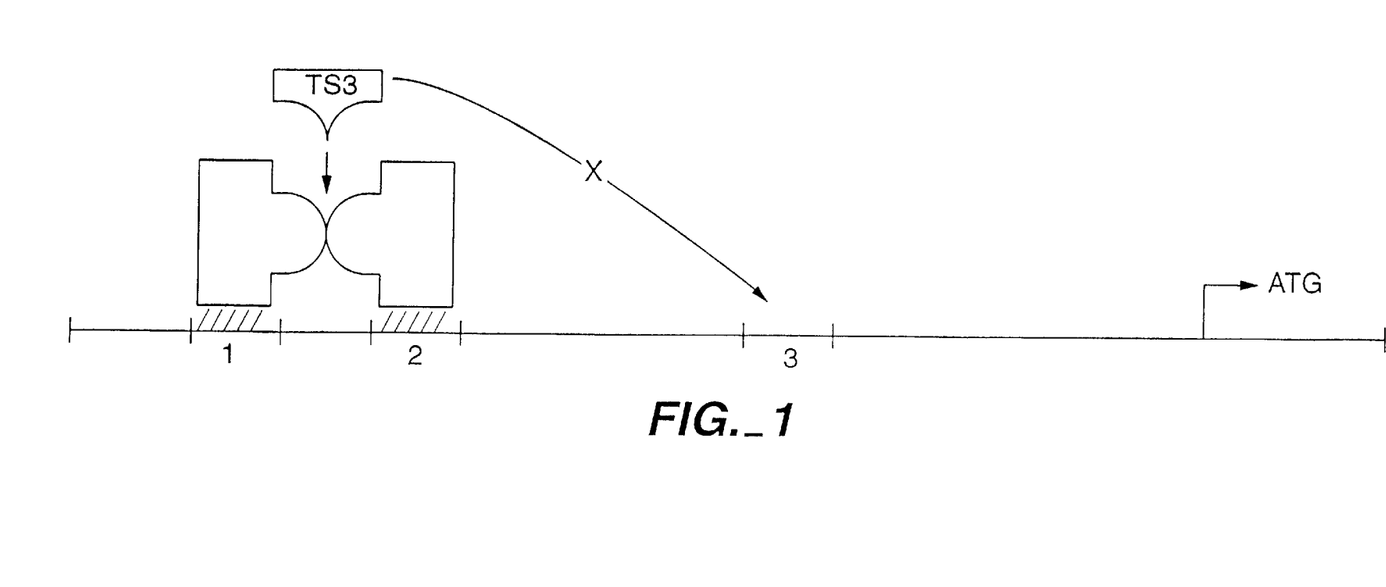
FIG. 1 is a schematic illustration of an embodiment of the method of the present invention. Specifically, a target gene has three cis-regulatory DNA sequence elements "1, 2 and 3" and a transcription termination sequence "ATG" wherein a light-chain containing antibody derivative and a complementary heavy chain containing antibody derivative specifically recognize and bind to adjacent cis-regulatory DNA sequence elements 1 and 2, respectively. Once bound, the antibody variable regions of the complementary antibody derivative molecules interact to form an antibody binding site for the transcription factor ("TS3")which recognizes and binds to cis-regulatory DNA sequence element number 3, thereby effectively competing for binding to cis-regulatory DNA sequence element 3.

The terms "transcription factor", "transcription factor protein" or grammatical equivalents herein means one of the many proteins involved in the transcriptional regulation of DNA and genes. Most transcription factors have at least two regions: (1) a region that recognizes and binds to a specific regulatory DNA sequence element that is associated with a gene and (2) a region that is responsible for altering the transcriptional expression of that gene. Thus, the term "transcription factor" is intended to encompass all proteins which recognize and specifically bind to cis-regulatory DNA sequence elements of a gene, wherein the binding of those transcription factors to those cis-regulatory DNA sequence elements has the effect of altering the transcriptional expression of that specific gene.

Transcription factor proteins generally produce their effects on the expression of a gene by binding to specific cis-regulatory DNA sequence elements which are associated with that gene. The interaction between transcription factor proteins and cis-regulatory DNA sequence elements provides for, at least in part, the regulatory control of expression of the gene, i.e., determines whether the gene is being actively expressed or not. Thus, as used herein, the phrase "cis-regulatory DNA sequence element" or grammatical equivalents thereof means the specific DNA sequence elements that are associated with a gene of interest and which are recognized and bound by specific transcription factor proteins to alter the expression of that gene. For the most part, cis-regulatory DNA sequence elements are specifically recognized and bound by only one specific transcription factor protein, however, two or more transcription factor proteins may recognize and bind to a single specific cis-regulatory DNA sequence element.

Cis-regulatory DNA sequence elements are well known in the art and are generally located in the region of a gene which is 5' to the transcription initiation site, however, cis-regulatory DNA sequence elements may also be located at various other sites in association with a gene, for example, 3' to the translation termination site or within the gene coding region itself. Cis-regulatory DNA sequence elements may vary in size, but generally are from between 5–30 base pairs in length.

The individual cis-regulatory DNA sequence elements of a gene may be "closely-apposed" or be separated by large amounts of intervening DNA. By "closely-apposed" is meant that the individual cis-regulatory DNA sequence elements are in close physical proximity to one another, specifically, in sufficiently close physical proximity where binding of complementary antibody derivative molecules of the present invention at those sites will result in an interaction between the variable regions of those complementary antibody derivative molecules and the formation of an antibody binding site for a transcription factor protein. By "adjacent" is meant that two individual cis-regulatory DNA sequence elements are not only "closely-apposed", but also are not separated by another intervening cis-regulatory DNA sequence element.

Assuming a specific eukaryotic gene possesses three individual cis-regulatory DNA sequence elements, since transcription factors recognize cis-regulatory DNA sequence elements with very high specificity, the combinatorial specificity of the three individual sites adequately defines the gene. If n1, n2 and n3 are the numbers of base pairs in the cis-regulatory DNA sequence element required for binding of the three transcription factors, for example, the probability that this set of target sites will appear on a random basis, i.e., specificity (S), is $G(4^{-n1} \cdot 4^{-n2} \cdot 4^{-n3})$, where G is the genome size, and n is typically between 6 and 9. If and only if all three sites are used, the gene is specially recognized. Only those other genes that utilize the exact same molecule will be recognized. If, for example n=8, for the human genome, $S=1.2\times10^{-5}$. Since only that fraction of G that is involved in cis-regulatory systems is properly included in this calculation (probably less than 10% of the DNA), S is probably $\sim10^{-6}$. Even if only two sites are utilized, S is still less than 0.1. Thus, it is extremely unlikely that a sequence specific DNA binding protein will bind to the wrong place.

Transcription factor proteins generally recognize and bind to a specific cis-regulatory DNA sequence element through a portion of the transcription factor protein called the "DNA binding domain". As used herein, the phrase "DNA binding domain" refers to the portion of any DNA binding protein which is sufficient for specific binding to a particular cis-regulatory DNA sequence element. Generally, the DNA binding domain of an antibody derivative molecule of the present invention will have the same native amino acid sequence as is possessed by that domain in the DNA binding protein from which it was derived. Those of ordinary skill in the art, however, will readily recognize that some differences in the native amino acid sequence of the DNA binding domain can be tolerated without significant loss of the ability to specifically recognize and bind to a particular cis-regulatory DNA sequence element. As such, substitutional, insertional and deletional variants of native DNA binding domains are also within the scope of the present invention and are encompassed within the phrase "DNA binding domain".

Substitutional variants are those that have at least one amino acid residue in a native sequence removed and a different amino acid inserted in its place at the same position. The substitutions may be single, where only one amino acid in the DNA binding domain has been substituted, or they may be multiple, where two or more amino acids have been substituted in the same DNA binding domain. Such substitutions are preferably made in accordance with the following Table 1 when it is desired to modulate finely the functional characteristics of a protein molecule.

TABLE 1

| Original Residue | Exemplary Substitutions |
| --- | --- |
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |

TABLE 1-continued

| Original Residue | Exemplary Substitutions |
| --- | --- |
| Tyr (Y) | trp; phe |
| Val (V) | ile; leu |

Substantial changes in function are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in polypeptide functional properties will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (e) a residue having an electronegative side chain is substituted for (or by) a residue having an electropositive charge; or (f) a residue having a bulky side chain, e.g., phenylalanine, is substituted for (or by) one not having such a side chain, e.g., glycine.

Insertional variants are those with one or more amino acids inserted immediately adjacent to an amino acid at a particular position in a native DNA binding domain sequence. Immediately adjacent to an amino acid means connected to either the α-carboxy or α-amino functional group of the amino acid.

Deletional variants are those with one or more amino acids in the native DNA binding domain sequence amino acid sequence removed. Ordinarily, deletional variants will have one or two amino acids deleted in a particular region of the DNA binding domain.

Substitutional, insertional and deletional variants of the DNA binding domain will not significantly affect the ability of that DNA binding domain to specifically recognize and bind to its respective cis-regulatory DNA sequence element. Those of ordinary skill in the art will readily know how to produce and identify DNA binding domain variants which retain the ability to specifically recognize and bind to their respective cis-regulatory DNA sequence elements. For example, amino acid variants of a DNA binding domain can be routinely prepared by obtaining a nucleic acid encoding a native DNA binding domain and subjecting that nucleic acid to either site-directed or random mutagenesis techniques which are well-known in the art. Expression of the mutagenized nucleic acid in an appropriate expression system, therefore, will yield the DNA binding domain variant. The variant DNA binding domain can be expressed either a hybrid polypeptide or unassociated with any other heterologous polypeptide sequences and can be assayed for its ability to recognize and bind to a specific cis-regulatory DNA sequence element by employing well-known competition binding assays. In such assays, a DNA template comprising the cis-regulatory DNA sequence element can be employed as a binding target for the variant DNA binding domain and native DNA binding domain and/or unrelated polypeptides can be employed as competitors of binding to the cis-regulatory DNA sequence element.

"Amino acid variants" include all substitutional, insertional and deletional variants of a polypeptide sequence which retain substantially the same functional characteristics as the native polypeptide.

When bound to a specific cis-regulatory DNA sequence element, transcription factor proteins may alter the expression of the gene with which those regulatory sequences are associated by either increasing or decreasing the expression of that gene. Thus, in the presence of antibody derivative molecules, the term "alter expression" or grammatical equivalents thereof means that the transcriptional activity of the gene is either increased or decreased as compared to the expression of the gene in the absence of antibody derivative molecules. Transcription factor proteins which function to increase transcription of a gene when bound to their specific cis-regulatory DNA sequence elements are "positive regulators" of the expression of that gene. Transcription factor proteins which function to decrease transcription of a gene when bound to their specific cis-regulatory DNA sequence elements are "negative regulators" of the expression of that gene.

The terms "antibody derivative", "antibody derivative molecule" or grammatical equivalents thereof refer to a hybrid protein molecule which possesses the ability to recognize and bind to a specific cis-regulatory DNA sequence element of a particular gene and, when bound thereto, possesses the ability to interact with a complementary antibody derivative which is bound to an adjacent cis-regulatory DNA sequence element to form an antibody binding site for a transcription factor protein. Specifically, the antibody derivatives of the present invention possess an N-terminal nuclear localization signal linked to either a light chain or heavy chain variable region of an antibody, wherein the antibody from which the variable region is derived is capable of specifically binding to a transcription factor protein, which is in turn linked to a C-terminal DNA binding domain that is derived from a protein that recognizes and binds to a specific cis-regulatory DNA sequence element. As such, one embodiment of the hybrid antibody derivative molecules of the present invention have the structure $NH_2$—NL—$VR_{LC/HC}$—DBD—COOH, where "$NH_2$" is the amino terminus of the antibody derivative molecule, "NL" is the nuclear localization signal, "$VR_{LC/HC}$" is the light chain or heavy chain variable region which is derived from an antibody capable of specifically binding to a transcription factor protein "DBD" is the DNA binding domain derived from a protein which specifically recognizes and binds to a cis-regulatory DNA sequence element and "COOH" is the carboxy terminus of the antibody derivative protein.

By "N-terminal nuclear localization signal" is meant a nuclear localization signal which is placed at or near the N-terminal end of the antibody derivative molecule. Various nuclear localization signals which may find use are well known in the art. By "C-terminal DNA binding domain" is meant a DNA binding domain which is placed at or near the C-terminal end of the antibody derivative molecule.

Thus, for example, a first antibody derivative molecule may comprise an N-terminal nuclear localization signal linked to a light chain variable region derived from an antibody that specifically binds to a transcription factor protein which is, in turn, linked to a C-terminal DNA binding domain derived from a protein that recognizes and binds to a cis-regulatory DNA sequence element of a gene. A second antibody derivative molecule may comprise an N-terminal nuclear localization signal linked to a heavy chain variable region which is derived from the same antibody described above that is, in turn, linked to a C-terminal DNA binding domain derived from a protein that binds to a cis-regulatory DNA sequence element which adjacent to the cis-regulatory DNA sequence element that is bound by the first antibody derivative molecule. When the first and second antibody derivative molecules are bound at their respective cis-regulatory DNA sequence elements, the light chain variable region of the first antibody derivative molecule and the heavy chain variable region of the second antibody derivative molecule interact to form an antibody binding site for a transcription factor protein which normally binds to a third cis-regulatory DNA sequence element. This newly-formed antibody binding site then competes with the third cis-regulatory DNA sequence element for binding to the transcription factor protein. Such competition effectively reduces the ability of the transcription factor protein to bind to its respective third cis-regulatory DNA sequence element, thereby altering the expression of the gene with which that element is associated. A schematic illustration of this method is presented in FIG. 1. The term "specific binding" refers to the phenomenon wherein a polypeptide molecule recognizes and binds to a specific DNA sequence or other binding entity but substantially does not recognize or bind to any other specific DNA sequence or other binding entity.

Optionally, the hybrid antibody derivative molecules of the present invention may also comprise a "linking polypeptide" which serves to connect and separate the antibody variable region of the antibody derivative molecule from the C-terminal DNA binding domain thereof. The linking polypeptide will be of sufficient length and flexibility so as to not substantially interfere with the function of the antibody variable region and the DNA binding domain of the antibody derivative molecule. The linking polypeptide will generally be from about 1 to about 50 amino acids in length, preferably from about 5 to about 20 amino acids in length and more preferably from about 5 to about 10 amino acids in length. The linking polypeptide can be inserted into the antibody derivative molecule by employing standard recombinant DNA techniques which are well known in the art.

Ordinarily, the terms "amino acid" and "amino acids" refer to all naturally occurring L-α-amino acids. In some embodiments, however, D-amino acids may be present in the antibody derivatives of the present invention in order to facilitate conformational restriction. For example, in order to facilitate disulfide bond formation and stability, a D-amino acid cysteine may be provided at one or both termini of an antibody derivative of the present invention. The amino acids are identified by either the single-letter or three-letter designations:

| | | | | | |
|---|---|---|---|---|---|
| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

The antibody derivatives of the present invention may also optionally comprise an antigenic epitope which is capable of being quantitatively detected in the nucleus of a eukaryotic cell. As such, the antigenic epitope may serve as a means for quantitatively measuring the amount of antibody derivative present in the nucleus of a cell. For the most part, antigenic epitopes which find use will be those that are recognized by well known and commercially available monoclonal antibodies for quantitative assessment. Antigenic epitopes which find use include, for example, c-myc, and the like. The antigenic epitope can be introduced into the antibody derivative molecule by employing standard recombinant DNA techniques which are well known in the art. The antigenic epitope may be placed at various locations in the antibody derivative molecule such that its presence does not affect functionality of the molecule, however, it is preferably placed between the N-terminal nuclear localization signal and the antibody variable region.

Nucleic acids encoding the antibody derivative molecules of the present invention are introduced into eukaryotic cells in such a manner so as to ensure that the expressed antibody derivative molecules can form the requisite transcription factor antibody binding site and effectively compete for binding to their respective cis-regulatory DNA sequence elements with the DNA binding proteins which normally bind to those cis-regulatory DNA sequence elements. Usually, each antibody derivative molecule is present in the nucleus of the cell at a concentration which is about 3 to about 30 times, preferably about 15 to about 30 times, the normal concentration of the DNA binding protein which binds to the same cis-regulatory DNA sequence element as does the antibody derivative. The presence of excess antibody derivative ensures that it will effectively compete with its respective endogenous DNA binding protein and will, therefore, bind to its specific cis-regulatory DNA sequence element.

Methods for increasing or decreasing the expression of an antibody derivative molecule from an expression vector and, therefore, modulating the concentration of antibody derivative in the nucleus of the cell are well known in the art. For example, numerous inducible promoters are known in the art and can be employed in an expression vector to modulate the amount of antibody derivative being expressed from that vector. Moreover, it is well known that certain nuclear localization signals are more efficient than others, thereby providing a means by which the skilled artisan can readily choose a nuclear localization signal which will provide for the desired concentration of antibody derivative in the nucleus.

"Antibodies (Abs)" and "immunoglobulins (Igs)" are glycoproteins having the same structural characteristics. Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al. (1985) *J. Mol. Biol.* 186:651–663; Novotny and Haber (1985) *Proc. Natl. Acad. Sci. USA* 82:4592–4596).

The term "variable domain" means the entire variable domain of an antibody light or heavy chain, or any fragment or amino acid variant thereof, which, when complexed with its corresponding heavy or light chain variable domain, is sufficient for specific binding to the antigenic entity to which the antibody from which the variable domains were derived is specifically directed.

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E. A. et al. (1991) *Sequences of Proteins of Immunological Interest*, National Institute of Health, Bethesda, Md.).

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The light chains of antibodies (immunoglobulins) from any vertebrate species can be assigned to one of two clearly distinct types, called kappa (κ) and lambda (λ). based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein (1975) *Nature* 256:495, or may be made by recombinant DNA methods (see, e.g. U.S. Pat. No. 4,816,567 (Cabilly et al.)).

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

"Oligonucleotides" are short-length, single- or double-stranded polydeoxynucleotides that are chemically synthesized by known methods, such as phosphotriester, phosphite, or phosphoramidite chemistry, using solid phase techniques such as those described in EP 266,032, published May 4, 1988, or via deoxynucleoside H-phosphonate intermediates as described by Froehler et al. (1986) *Nucl. Acids Res.* 14:5399. They are then purified on polyacrylamide gels.

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5× SSC (0.75 M NaCl, 0.075 M sodium citrate), 50 mM sodium phosphate (pH 6/8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2× SSC and 0.1% SDS. Yet another example is hybridization using a buffer of 10% dextran sulfate, 2× SSC (sodium chloride/sodium citrate) and 50% formamide at 55° C., followed by a high-stringency wash consisting of 0.1× SSC containing EDTA at 55° C.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered.

"Transformation" means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described by Cohen, S. N. (1972) *Proc. Natl. Acad. Sci.* (*USA*) 69:2110 and Mandel et al. (1970) *J. Mol. Biol.* 53:154, is generally used for prokaryotes or other cells that contain substantial cell-wall barriers. For mammalian cells without such cell walls, the calcium phosphate precipitation method of Graham, F. and van der Eb, a. (1978) *Virology* 52:456–457 is preferred. General aspects of mammalian cell host system transformations have been described by Axel in U.S. Pat. No. 4,399,216 issued Aug. 16, 1983. Transformations into yeast are typically carried out according to the method of Van Solingen, P., et al. (1977) *J. Bact.*, 130:946 and Hsiao, C. L., et al. (1979) *Proc. Natl. Acad. Sci.* (*USA*) 76:3829. However, other methods for introducing DNA into cells such as by nuclear injection, electroporation or by protoplast fusion may also be used.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al. (1981) *Nucleic Acids Res.* 9:6103–6114 and D. Goeddel et al. (1980) *Nucleic Acids Res.* 8:4057.

"Ligation" refers to the process of forming phosphodiester bonds between two double stranded nucleic acid fragments (T. Maniatis et al. (1982) supra, p. 146). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis et al. (1982) supra, p. 90, may be used.

B. General Methodology

1. Preparation of Expression Vectors

After a eukaryotic gene of interest has been chosen as a target for the antibody derivative molecules of the present invention, one may routinely identify and clone nucleic acids encoding the transcription factor proteins which bind to the cis-regulatory DNA sequence elements of that eukaryotic gene. The method of the present invention requires that the target gene possess at least three cis-regulatory DNA sequence elements which are involved in the transcriptional regulation of the target gene. Once a target gene has been chosen, one may employ well-known affinity chromatography or Western blot analyses to identify, purify and clone the transcription factor proteins which specifically recognize and bind to the at east three cis-regulatory DNA sequence elements of the target gene. Moreover, numerous DNA binding transcription factors and the cis-regulatory DNA sequence elements to which they bind have already been identified and cloned, many of which will be useful in the method described herein.

By employing well-known mutagenesis techniques, such as site-directed or random mutagenesis, one may obtain variants of the cloned transcription factor proteins and by employing these variants in in vitro assays designed to measure the ability of the variant to bind to its specific cis-regulatory DNA sequence, one can determine which amino acids of the transcription factor protein are sufficient for recognition and binding to its specific cis-regulatory DNA sequence element. In this manner, one may routinely identify and clone the nucleic acid sequences encoding the DNA binding domains of two transcription factor proteins which recognize and bind to adjacent first and second cis-regulatory DNA sequence elements of the target gene. The nucleic acid sequences encoding these DNA binding domains can be obtained from nucleic acid sequences encoding the full length transcription factor or may be chemically synthesized by well known methods.

Next, monoclonal antibodies are prepared which are directed against a transcription factor protein which specifically recognizes and binds to a third cis-regulatory DNA sequence element of the target gene. For example, anti-transcription factor monoclonal antibodies may be made using the hybridoma method first described by Kohler & Milstein (1975) *Nature* 256:495, or may be made by recombinant DNA methods (Cabilly, et al., U.S. Pat. No. 4,816, 567).

DNA encoding the anti-transcription factor monoclonal antibodies is readily isolated and sequenced using conventional procedures (e.g., by using oligonucleotide probes that are capable of binding specifically to genes encoding the heavy and light chains of murine antibodies). Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

Monoclonal antibody isolates generated as described above are then incubated with recombinant transcription factor protein in vitro and those which specifically bind to the transcription factor protein are identified by supershift activity on non-reducing polyacrylamide gels. a cDNA library is then made from the cell line producing the selected monoclonal antibody, the cDNA library is screened for clones encoding both the light and heavy chains of the selected monoclonal antibody and the clones are sequenced to confirm that full length clones have been obtained. Methodology for generating and screening cDNA libraries as well as sequencing the identified clones is available and well known in the art.

Optionally, the activity of the polypeptides encoded by the full length light chain and heavy chain clones is determined by expressing the polypeptides encoded by the clones, reassembling the antibody subunits encoded by the light and heavy chain clones in vitro and testing the reassembled protein for supershift activity on non-reducing polyacrylamide gels when incubated with recombinant transcription factor in vitro.

Once the full length light chain and heavy chain clones are isolated, nucleic acid encoding an appropriate nuclear localization signal is ligated to the 5' end of the light or heavy chain coding sequence. Ligation is carried out such that the coding sequences of the nuclear localization signal and the antibody light or heavy chain are in frame with one another. Optionally, nucleic acid encoding an antigenic epitope which can be used to quantify the amount of the molecule in the cell nucleus can also be ligated into the construct, preferably between the nuclear localization signal and the light or heavy chain sequences. The preparation of these constructs employs standard recombinant DNA techniques which are readily available and well known in the art.

Again, the constructs are sequenced and the nucleic acid encoding the constant region of the full length light and heavy chains is deleted, thereby resulting in constructs encoding an N-terminal nuclear localization signal linked in frame to the light chain or heavy chain variable region of an antibody which specifically binds to a target transcription factor protein. To the 3' end of the sequences encoding the light or heavy chain variable regions, an oligonucleotide may optionally be ligated which encodes a linking polypeptide of appropriate length.

Nucleic acid sequences encoding the DNA binding domains of the transcription factor proteins which specifically recognize and bind to the first and second cis-regulatory DNA sequence elements (obtained as described above) are then ligated to the 3' end of the nucleic acid sequences encoding the heavy and light chain variable regions (or linking polypeptide if one exists). Such ligation results in two expression constructs, the first encoding an antibody derivative molecule having the structure $NH_2$—NL—$V_{LC}$—DBD—COOH and the second encoding an antibody derivative molecule having the structure $NH_2$—NL—$V_{HC}$—DBD—COOH where "$NH_2$" is the amino terminus of the antibody derivative molecule, "NL" is the nuclear localization signal, "$V_{LC}$" is the light chain variable region, "$V_{HC}$" is the heavy chain variable region, "DBD" is the DNA binding domain and "COOH" is the carboxy terminus of the antibody derivative molecule. As described above, the construct may also optionally encode an antigenic epitope and/or a linking polypeptide. Thus, the final construct encode embodiments of the antibody derivative molecules of the present invention.

The above described constructs can also be modified to include various promoters, enhancer sequences and the like so as to be useful for a variety of different applications. The ordinarily skilled artisan will well know how to modify and adapt such constructs for optimal efficiency.

2. Introduction of Expression Vectors into Cells and Altering Transcription

The above described expression vectors encoding the antibody derivative molecules of the present invention are then introduced into target cells by any one of a variety of methods. For example, the expression vectors encoding the antibody derivative molecules may be introduced into target cells using any one of a variety of different benign virus delivery vehicles which are well known in the art. Such vehicles include poxviruses, herpesviruses, adenoviruses, papovaviruses, retroviruses, alphaviruses, myxoviruses, picornaviruses, and the like.

a further option for the introduction of the antibody derivative molecule-encoding expression vectors into target cells is through the use of encapsulated nucleic acid in liposomes or other lipid-based transfection agents. Techniques for the production and administration of the encapsulated nucleic acid have been described and are well known in the art.

Moreover, nucleic acid encoding the antibody derivative molecules of the present invention can be complexed with proteins which are specific for cellular uptake by a specific type of cell or cells. For example, complexing the nucleic acid to various cell surface receptor binding proteins has proven an efficient means for introducing nucleic acid into a target cell.

Also, it has also been reported that injection of free plasmid DNA directly into body tissues such as skeletal muscle or skin can result in cellular uptake of the plasmid DNA and expression of the polypeptides encoded by that DNA in cells. Ulmer et al. (1993) *Science* 259:1745–1749, Wang et al. (1993) *Proc. Natl. Acad. Sci. USA* 90:4156–4160 and Raz et al. (1994) *Proc. Natl. Acad. Sci. USA* 91:9519–9523.

Once the above described expression vectors are introduced into the target cells, the antibody derivative molecule encoded thereby are expressed, transported to the nucleus via the N-terminal nuclear localization signal and bind, via their specific DNA binding domains, to their specific adjacent first and second cis-regulatory DNA sequence elements. Once bound to the adjacent cis-regulatory DNA sequence elements, the antibody derivative molecules interact to form an antibody binding site for a transcription factor that is capable of affecting transcription of the target gene by binding to a third cis-regulatory DNA sequence element. This newly formed antibody binding site competes with the third cis-regulatory DNA sequence element for binding to the transcription factor, thereby exerting an effect on transcription of the target gene.

C. Uses for antibody derivatives molecules

The methods and compositions of the present invention are useful for a variety of different applications. For example, the antibody derivative molecules of the present invention and methods of using them are useful for altering the transcriptional expression of a gene of interest. Having an available means for altering the transcriptional expression of a gene of interest has a variety of in vivo applications including, for example, the therapeutic treatment of viral diseases, cancer or any other disease associated with a mis-regulation of gene expression. Moreover, the present invention will find use in the modulation of gene expression for the advancement of biotechnological research in a variety of different areas. Also apparent are research applications for the purpose of determining gene function or the function of specific cis-regulatory DNA sequence elements or trans-acting protein factors.

Thus, the present invention is useful for affecting the expression of a specific gene in vivo without affecting virtually all other genes.

The antibody derivative molecules of the present invention are also useful as competitive antagonists for the binding of specific transcription factor proteins to their specific cis-regulatory DNA sequence elements. Moreover, the antibody derivative molecules of the present invention will find use for identifying novel cis-regulatory DNA sequence elements which are related to the specific element to which the antibody derivative molecule is specifically directed.

D. Concluding Remarks:

The foregoing description details specific methods which can be employed to practice the present invention. Having detailed such specific methods, those skilled in the art will well enough know how to devise alternative reliable methods at arriving at the same information in using the fruits of the present invention. Thus, however detailed the foregoing may appear in text, it should not be construed as limiting the overall scope thereof; rather, the ambit of the present invention is to be determined only by the lawful construction of the appended claims. All documents cited herein are hereby expressly incorporated by reference.

What is claimed is:

1. An antibody derivative molecule that specifically binds to a first cis-regulatory DNA sequence element of a eukaryotic gene, said antibody derivative molecule comprising:
   (a) an N-terminal nuclear localization signal;
   (b) a variable region of an antibody molecule, wherein said antibody molecule specifically binds to a transcription factor protein and wherein said transcription factor protein specifically binds to a second cis-regulatory DNA sequence element of said gene; and
   (c) a C-terminal DNA binding domain derived from a protein that specifically binds to said first cis-regulatory DNA sequence element.

2. The antibody derivative molecule according to claim 1 wherein said variable region is a light chain variable region.

3. The antibody derivative molecule according to claim 1 wherein said variable region is a heavy chain variable region.

4. The antibody derivative molecule according to claim 1 further comprising a linking polypeptide which serves to connect said variable region and said C-terminal DNA binding domain.

5. The antibody derivative molecule according to claim 1 further comprising an antigenic epitope that can be quantitatively detected in the nucleus of a eukaryotic cell.

6. The antibody derivative molecule according to claim 5 wherein said antigenic epitope is located between said N-terminal nuclear localization signal and said variable region.

7. The antibody derivative molecule according to claim 5 wherein said antigenic epitope is c-myc.

* * * * *

UNITED STATES PATENT AND TRADEMARK OFFICE
CERTIFICATE OF CORRECTION

PATENT NO : 5,994,512  
DATED : November 30, 1999  
INVENTOR(S) : DAVIDSON, ERIC H.

Page 1 of 2

It is certified that error appears in the above-identified patent and that said Letters Patent is hereby corrected as shown below:

On the title page,
Item [56] REFERENCES CITED

Column 1, first reference cited, following "*Biochemical and Biophysical Research Communication*", insert --,--.

Column 2, line 1, following "E.A., ", insert --"--.

Column 2, line 2, following "IgG", insert --"--.

Column 2, line 3 delete "ad" and insert therefore --and--

Column 2, lines 9 through 11, delete "Biocca et al. Expression and targetingt of intracellular antibodies in mammalian cells. EMBO J. vol. 9 pp. 101-108, (1990)."

Column 1, line 38, delete "depend ing upon" and insert therefore --depending upon--.

Column 1, line 40, delete "transcription al regulators" and insert therefore --transcriptional regulators--.

UNITED STATES PATENT AND TRADEMARK OFFICE
CERTIFICATE OF CORRECTION

PATENT NO : 5,994,512
DATED : November 30, 1999
INVENTOR(S) : DAVIDSON, ERIC H.

It is certified that error appears in the above-identified patent and that said Letters Patent is hereby corrected as shown below:

Column 1, line 46, delete "effort s have" and insert therefore --efforts have--.

Column 1, line 56, delete "express ion of more" and insert therefore --expression of more--.

Column 13, line 14, delete "a cDNA" and insert therefore --A cDNA--.

Column 14, line 25, delete "a further option" and insert therefore --A further option--.

Signed and Sealed this

Thirteenth Day of February, 2001

NICHOLAS P. GODICI

Attest:

Attesting Officer    Acting Director of the United States Patent and Trademark Office